United States Patent [19]

Suyama et al.

[11] Patent Number: 4,947,004

[45] Date of Patent: Aug. 7, 1990

[54] METHOD FOR PRODUCING 1,1,3,3-TETRAMETHYLBUTYL HYDROPEROXIDE

[75] Inventors: Shuji Suyama; Mitsukuni Kato, both of Aichi; Jun Takada, Chita; Hiroshi Okada, Tokoname, all of Japan

[73] Assignee: Nippon Oil and Fats Company, Ltd., Japan

[21] Appl. No.: 332,983

[22] Filed: Apr. 4, 1989

[30] Foreign Application Priority Data

Dec. 15, 1987 [JP] Japan ................................ 62-315181

[51] Int. Cl.$^5$ .......................................... C07C 179/02
[52] U.S. Cl. .................................................. 568/568
[58] Field of Search ................................ 568/568, 576

[56] References Cited

FOREIGN PATENT DOCUMENTS 680834 2/1964 Canada .

OTHER PUBLICATIONS

Organic Synthesis, vol. 40, pp. 76–79 (1960).
Journal of the American Chemical Society, vol. 77, Nov. 26, 1955, No. 22.
Journal of the American Chemical Society, vol. 77, May 12, 1955, No. 9.

Primary Examiner—Bruce Gray
Attorney, Agent, or Firm—Arnold, White & Durkee

[57] ABSTRACT

High-purity 1,1,3,3-tetramethylbutyl hydroperoxide can be easily and safely produced without the formation of dangerous acetone peroxide, by the reaction of neopentyldimethylcarbinol with hydrogen peroxide in the presence of sulfuric acid.

1 Claim, No Drawings

METHOD FOR PRODUCING 1,1,3,3-TETRAMETHYLBUTYL HYDROPEROXIDE

Background of the Invention (1) Field of the Invention:

This invention relates to an improve method for producing 1,1,3,3-tetramethylbutyl hydroperoxide (hereinafter, abbreviated as OHPO), and more particularly relates to a method for producing inexpensively OHPO having a high purity.

(2) Related Art Statement: There has hitherto been predominantly produced OHPO by a method, wherein diisobutylene is reacted with a mixture of sulfuric acid and hydrogen peroxide according to the following reaction equation:

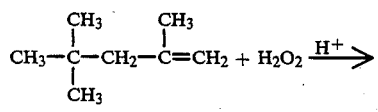

(diisobutylene)

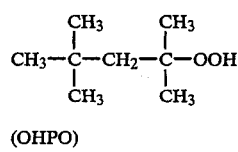

(OHPO)

A typical example of the above described reaction is described in Organic Synthesis, Vol. 40, pages 76–79 (1960). According to this reaction, 2 mols of diisobutylene is added to a mixture consisting of 7.06 mols of 30% hydrogen peroxide and 7.76 mols of 95% sulfuric acid, and the diisobutylene is reacted with the hydrogen peroxide at 25° C. for 24 hours to produce OHPO.

However, the above described method for producing OHPO from diisobutylene used as a starting material requires an excessively large amount of a mixture of sulfuric acid and hydrogen peroxide and further requires a very long reaction time. Moreover, the resulting OHPO is apt to be easily decomposed by acid and neopentyl alcohol and acetone are formed according to the following equation.

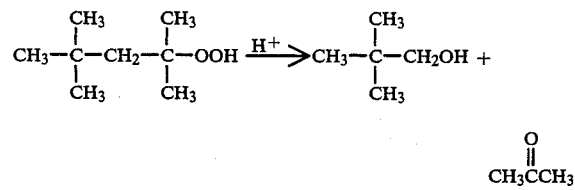

When a reaction of diisobutylene with a mixture of sulfuric acid and hydrogen peroxide is carried out for a long period time in order to enhance the rate of reaction, acetone is formed in an increased amount by the above described decomposition of OHPO, and acetone peroxide is formed by the reaction of acetone with the mixture of sulfuric acid and hydrogen peroxide (Journal of the American Chemical Society, Vol. 77, page 3139, (1955)). This acetone peroxide is once dissolved in liquid OHPO, but is deposited in the form of crystal with the lapse of time. The acetone peroxide deposited in the form of crystal is very sensitive to rubbing and shock and has a very strong power at the explosion (Journal of the American Chemical Society, Vol. 77, page 6073 (1955)). Therefore, the formation of acetone peroxide crystal is a serious problem in the handling. Accordingly, there has been eagerly demanded to develop a method for producing a high-purity OHPO containing no acetone peroxide in a short reaction time.

The inventors have variously investigated, and found out that the above described drawbacks can be eliminated by using neopentyldimethylcarbinol (hereinafter, abbreviated as DIB-OH) as a starting material, and accomplished the present invention.

SUMMARY OF THE INVENTION

The feature of the present invention lies in a method for producing high-purity OHPO containing no acetone peroxide in a short reaction time by reacting DIB-OH or diisobutylene containing DIB-OH with hydrogen peroxide in the presence of sulfuric acid.

DESCRIPTION OF THE PREFERRED EMBODIMENT

In the present invention, DIB-OH is used alone or in admixture with diisobutylene. The mixture of DIB-OH and diisobutylene must contain at least 50% by weight of DIB-OH. When the mixture contains less than 50% by weight of DIB-OH, the reaction velocity is low and it is difficult to obtain high-purity OHPO in a short reaction time.

The reaction is preferably carried out by a method, wherein DIB-OH or diisobutylene containing DIB-OH is dropwise added to a mixture of sulfuric acid and hydrogen peroxide.

In general, sulfuric acid is used in an amount of 0.5–2 mols and hydrogen peroxide is used in an amount of 1–3 mols based on 1 mol of DIB-OH, and the concentration of sulfuric acid in the mixture of sulfuric acid and hydrogen peroxide is adjusted to be 38–45% by weight. When a mixture of DIB-OH and diisobutylene is used, sulfuric acid and hydrogen peroxide are used in the above described amounts based on 1 mol of the sum of mols of DIB-OH and diisobutylene.

The reaction temperature is preferably 0°–30° C. When the temperature is lower than 0° C., the reaction velocity is low, and when the temperature is higher than 30° C., the temperature control is difficult due to heat generation, and is not advantageous for commercial purpose.

The feature of the use of a starting material of DIB-OH in the method for producing OHPO in the present invention lies in that high-purity OHPO containing no acetone peroxide can be produced in a short reaction time as compared with a conventional method for producing OHPO by the use of diisobutylene. Therefore, according to the present invention, OHPO can be produced inexpensively by an easy handling.

The present invention will be explained in more detail referring to the following examples and comparative examples.

Example 1

Into a four-necked flask of 200 ml capacity equipped with a thermometer, a dropping funnel and a stirrer was charged 40.8 g (0.6 mol) of 50% hydrogen peroxide, and then while cooling the flask from the exterior to keep the temperature in the interior of the flask to 10° C. or lower, 28 g (0.28 mol) of 98% sulfuric acid was dropwise added to the 50% hydrogen peroxide to prepare a mixture of sulfuric acid and hydrogen peroxide (the concentration of sulfuric acid in the mixture: 39.9%). Then, the temperature of the mixture was kept to 10° C., and 65.1 g (0.5 mol) of DIB-OH was dropwise added to the mixture in 15 minutes, and further the resulting mixture was kept to 10° C. for 2 hours to continue the reaction. After completion of the reaction, the reaction mixture was poured into a separating funnel, and an aqueous layer was separated off. The resulting organic layer was washed with water and then dried to obtain 70.1 g of a reaction product. When the active oxygen content in the reaction product was measured by the iodometry, the active oxygen content in the reaction product was found to be 9.86%, which showed that the purity of the product calculated as OHPO was 90.1% (theoretical active oxygen content in OHPO: 10.94%), and that the yield was 86.4% based on the theoretical yield. Even when the reaction product was stored in an incubator at 0° C. for 1 month, the crystal of acetone peroxide was not deposited.

EXAMPLES 2-4 AND COMPARATIVE EXAMPLES 1 AND 2

The same reaction as described in Example 1 was carried out, except that a mixture of DIB-OH and diisobutylene in a mixing ratio shown in the following Table 1 was used as a starting material in place of DIB-OH. The resulting reaction product was purified in the same manner as described in Example 1, and the purity and yield of the product were measured. Further, whether the crystal of acetone peroxide was deposited or not was observed.

The obtained results are shown in the following Table 2.

TABLE 1

|  | DIB-OH (g (mol)) | Diisobutylene (g (mol)) | Content of DIB-OH (wt %) |
|---|---|---|---|
| Example 2 | 52.1 (0.40) | 11.2 (0.10) | 82.3 |
| Example 3 | 45.6 (0.35) | 16.8 (0.15) | 73.0 |
| Example 4 | 32.6 (0.25) | 28.1 (0.25) | 53.7 |
| Comparative example 1 | 28.7 (0.22) | 31.4 (0.28) | 47.7 |
| Comparative example 2 | — | 56.1 (0.50) | 0 |

TABLE 2

|  | Amount of reaction product (g) | Active oxygen content (%) | Purity (%) | Yield (%) | Deposition of acetone peroxide crystal |
|---|---|---|---|---|---|
| Example 2 | 69.3 | 9.70 | 88.7 | 84.1 | none |
| Example 3 | 70.9 | 9.30 | 85.3 | 82.7 | none |
| Example 4 | 71.5 | 9.11 | 83.3 | 81.4 | none |
| Comparative example 1 | 70.6 | 8.04 | 73.5 | 71.0 | none |
| Comparative example 2 | 63.9 | 1.65 | 15.1 | 13.2 | none |

It can be seen from the results shown in Table 2 that, when the starting mixture has a content of DIB-OH of less than 50%, the reaction velocity is low, and it is difficult to obtain high-purity OHPO in a high yield. Further, it can be seen that the reaction of diisobutylene alone is very slow, and is disadvantageous in view of the commercial production of OHPO. In all of the reaction products, acetone peroxide did not deposit. In Comparative example 2 also, acetone peroxide did not deposit. The reason is probably that the reaction was not fully proceeded and the amount acetone formed by the decomposition of OHPO was small. EXAMPLES 5 and 6

In a four-necked flask of 300 ml capacity equipped with a thermometer, a dropping funnel and a stirrer was prepared a mixture of sulfuric acid and hydrogen peroxide in a mixing ratio shown in the following Table 3, then 65.1 g (0.5 mol) of DIB-OH was dropwise added to the mixture, and then DIB-OH was reacted with hydrogen peroxide for 1 hour at a temperature shown in the following Table 3. The reaction product was treated in the same manner as described in Example 1. The obtained results are shown in the following Table 4.

TABLE 3

|  | 50% $H_2O_2$ (g (mol)) | 98% $H_2SO_4$ (g (mol)) | $H_2O$ (g) | Concentration of $H_2SO_4$ (%) | $H_2O_2/H_2SO_4$ DIB-OH (molar ratio) | Reaction temperature (°C.) |
|---|---|---|---|---|---|---|
| Example 5 | 68 (1.0) | 50 (0.5) | — | 41.5 | 2/1/1 | 30 |
| Example 6 | 102 (1.5) | 100 (1.0) | 31.3 | 42.0 | 3/2/1 | 25 |

TABLE 4

|  | Amount of reaction product (g) | Active oxygen content (%) | Purity (%) | Yield (%) | Deposition of acetone peroxide crystal |
|---|---|---|---|---|---|
| Example 5 | 70.5 | 10.22 | 93.4 | 90.1 | none |
| Example 6 | 70.1 | 10.35 | 94.6 | 90.7 | none |

COMPARATIVE EXAMPLE 3

A reaction was carried out in the same manner as described in Example 6, except that diisobutylene was used as a starting material in place of DIB-OH and the reaction time was 28 hours. The obtained result was as follows.

| Amount of reaction product | 70.6 g |
|---|---|
| Active oxygen content | 8.54% |
| Purity | 78.1% |
| Yield | 75.4% |
| Deposition of acetone peroxide crystal | Deposited after 5 days |

The deposited acetone peroxide crystal was separated by filtering the reaction product. When the amount of the separated acetone peroxide crystal was measured, it was found that the acetone peroxide crystal was contained in the reaction product in an amount of 3.5% by weight.

It can be seen from the result of the above described experiment that, when diisobutylene is used as a starting material, a very long reaction time is required in order to obtain OHPO having a commercially available high purity, and hence a decomposition reaction of the resulting OHPO occurs, and acetone peroxide is formed due to the decomposition of OHPO.

What is claimed is:

1. A method for producing 1,1,3,3-tetramethylbutyl hydroperoxide, comprising adding dropwise, at a temperature of 0–30° C. 1 mol of neopentyldimethylcarbinol alone or in the form of a mixture consisting of 100(exclusive)-50% by weight of neopentyldimethylcarbinol and less than 50% by weight of diisobutylene to an aqueous solution containing a mixture of 0.5–2 mols of sulfuric acid and 1–3 mols of hydrogen peroxide, whereby the neopentyldimethylcarbinol is reacted with the hydrogen peroxide in the presence of the sulfuric acid.

* * * * *